United States Patent [19]

Free

[11] 4,008,045
[45] Feb. 15, 1977

[54] ULTRA-VIOLET STERILIZER HAVING A FLUID FLOW DIFFUSER PLATE

[75] Inventor: David Free, Vancouver, Canada

[73] Assignee: Naturvard Research (Canada) Ltd., Vancouver, Canada

[22] Filed: Oct. 11, 1974

[21] Appl. No.: 514,269

[30] Foreign Application Priority Data

Oct. 3, 1974 Canada .............................. 210733

[52] U.S. Cl. ............................. 21/102 R; 21/103; 21/DIG. 2; 250/436; 250/437; 250/438
[51] Int. Cl.² ....................... A61L 3/00; A61L 3/02
[58] Field of Search ......... 21/91, 102 R, 103, 54 R, 21/DIG. 2; 250/436, 437, 438

[56] References Cited

UNITED STATES PATENTS

| | | | |
|---|---|---|---|
| 2,309,124 | 1/1943 | Knott | 250/437 |
| 2,338,388 | 1/1944 | Whitman | 250/436 |
| 2,501,290 | 3/1950 | Pequignot | 250/436 |
| 2,667,584 | 1/1954 | Rhodes | 21/102 R X |
| 3,456,107 | 7/1969 | Robertson | 21/102 R X |
| 3,527,940 | 9/1970 | Balanca et al. | 250/437 X |
| 3,731,090 | 5/1973 | Veloz | 250/437 |
| 3,836,781 | 9/1974 | Ellison | 250/436 X |
| 3,843,521 | 10/1974 | Zeff | 21/102 R X |

FOREIGN PATENTS OR APPLICATIONS 888,446  7/1949  Germany .............................. 21/102

*Primary Examiner*—Morris O. Wolk
*Assistant Examiner*—Bradley R. Garris
*Attorney, Agent, or Firm*—Finnegan, Henderson, Farabow & Garrett

[57] ABSTRACT

Enhanced efficiency of an ultra-violet water sterilization device is assured by disposing a diffuser plate constructed of vanes at one end of a sterilization device so that the liquid flows by the vanes, to become turbulent and is directed into a rotational, non channeled path through a sterilization flux such that the flow of incremental fluid through the device becomes essentially constant and predictable so that the exposure of incremental fluid to the sterilization flux can be controlled to ensure bacteria kill.

1 Claim, 4 Drawing Figures

ULTRA-VIOLET STERILIZER HAVING A FLUID FLOW DIFFUSER PLATE

This invention relates to a fluid flow diffuser plate particularly suitable for fluid sterilization chambers.

In fluid, particularly water, sterilization devices employing ultraviolet radiation as the source of "bacteriastat" energy (radiation which kills bacteria) a linear ultraviolet radiation tube is generally used to generate bacteriastat wave lengths of ultraviolet radiation. The ultraviolet radiation tube is generally mounted coaxially within a cylindrical chamber through which is allowed to flow a volume of fluid, which is to be sterilized, at a controlled rate of speed. Generally the speed of the fluid flow is controlled to ensure residence time of the fluid within the chamber sufficient in relation to the density of flux produced by the radiation tube to ensure a positive bacteria kill.

It has been known that if the rate of speed of the fluid flowing through the sterilization device is too great the fluid is not exposed to the bacteriastat radiation for sufficient duration for a kill. It has been common, as one expedient, to ensure bacteria kill, to increase the exposure time of the fluid to the bacteriastat radiation by decreasing the rate of fluid flow. Alternatively, by increasing the flux density of the bacteriastat radiation, bacteria kill may also be ensured. Both of these expedients reduce the efficiency and economy of the fluid sterilizer; reduction of the rate of flow decreases the total volume of fluid treated in a given time period; increasing flux density of the bacteriastat radiation increases the capital cost and operating cost of such a sterilizing device dramatically.

It has now been found that reduction of the rate of fluid flow through the sterilization device as mentioned, is not conclusive to ensure that all the fluid flowing through the device has been uniformly exposed to the bacteriastat radiation for the minimum residence time or duration required for bacteria kill. It has been found that some fluid flowing through the device, when not under a controlled turbulence and flow path within the chamber, will have a residence time within the chamber longer or shorter than others. This result is due to the fact, that normally, flow within the chamber may be not turbulent but laminar. This induces channeling of the fluid within the chamber resulting in the residence time, within the chamber, of incremental fluid not being consistent. This being the case, and in order to achieve positive bacteria kill for all fluid flowing through the chamber, the rate of flow must be reduced to such a degree that the incremental fluid which has the shortest retention time within the chamber, has a retention time sufficient to permit adequate exposure to the bacteriastat radiation for a duration to ensure a bacteria kill.

Thus, the mean residence time of the fluid within the chamber, during flow, is not the true criteria for ensuring a positive bacteria kill of the treated fluid. Hence the heretofore expedient to increase the mean residence time of the fluid within the chamber by reducing the rate of the fluid flow which did not necessarily modify the channeled fluid (incremented fluid) is inappropriate.

The invention, therefore, contemplates a device within a sterilization chamber whereby inflowing fluid is caused, by the device, to flow in a precise controlled flow path within the sterilization chamber during its flow movement therethrough.

Also contemplated is that all incremental fluid flowing through the device will flow during all conditions at a velocity where the retention time of the incremental fluid within the device is satisfied for bacteriastat kill and then ejected.

Particularly, the invention also contemplates that the device conduct the flow of the fluid in a non channelled, preferably turbulent manner whence the retention time of incremental fluid flowing through a flux of bacteriastat radiation is essentially constant and predictable. Where the bacteriastat radiation emanates from a coaxial source the flow path of the incremental fluid through the radiation flux should be helical.

The invention also contemplates that the device be a fluid flow diffuser plate mounted within the chamber.

The invention, therefore, achieves an improved fluid sterilization chamber including an outer cylindrical housing, a fluid inflow channel near one end and a fluid outflow channel near the other end, and a coaxially mounted radiation device, the improvement comprising a fluid flow deflector member within the chamber mounted near the inflow channel extending between the radiation device and the cylindrical housing said member including vane means for directing inflowing fluid into a rotational path as it passes over the member, preferably a turbulent rotational path.

The invention further achieves a liquid flow diffuser plate comprising a plurality of non-overlapping vanes mounted into a rigid annulus defining a central aperture whose diameter is at least one half of the exterior diameter of the annulus.

The invention will now be described by way of example with reference to the accompanying drawings in which FIG. 1 is a perspective view of an assembled sterilizer, partially sectioned, employing an embodiment of the invention.

Figure 1:
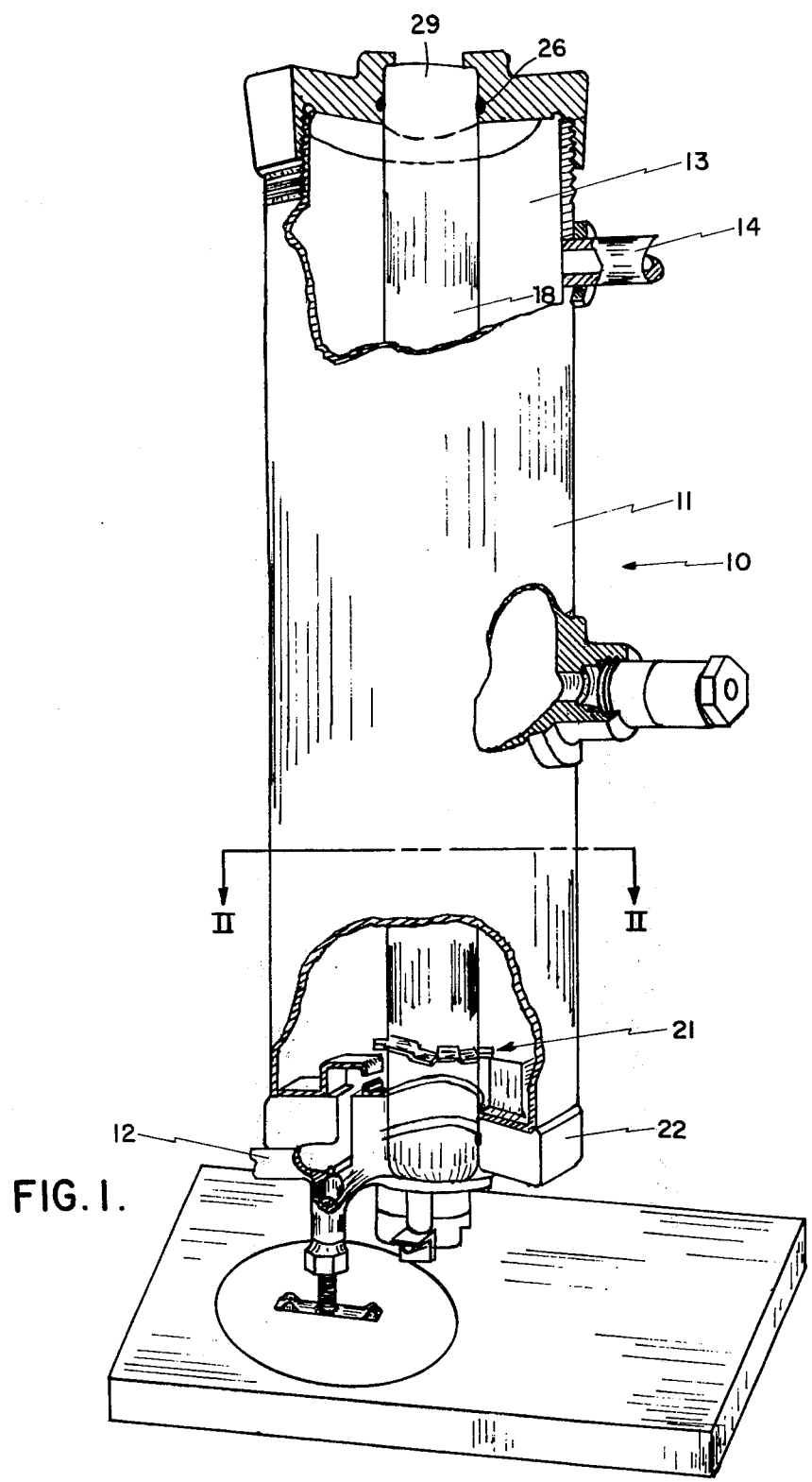

Referring to FIG. 1, the sterilization device 10 particularly a water sterilizer includes an outer cylindrical housing 11 and an inlet channel 12 communicating with an inner chamber 13 at one end and an outlet channel 14 at the other end of the housing. Coaxially mounted within the housing is an ultraviolet radiation tube 16, which acts, as a source of bacteriastat ultraviolet radiation. Surrounding the tube 16 and isolating it from the chamber 13 is a protective sheet 18 of silicate glass which permits ultra-violet radiation to be transmitted into the chamber 13 where fluid (water) is to be sterilized by its exposure to the bacteriastat wave lengths of ultraviolet radiation, while isolating the tube 16 from the temperature effects of the fluid in the chamber 13.

Figure 2:
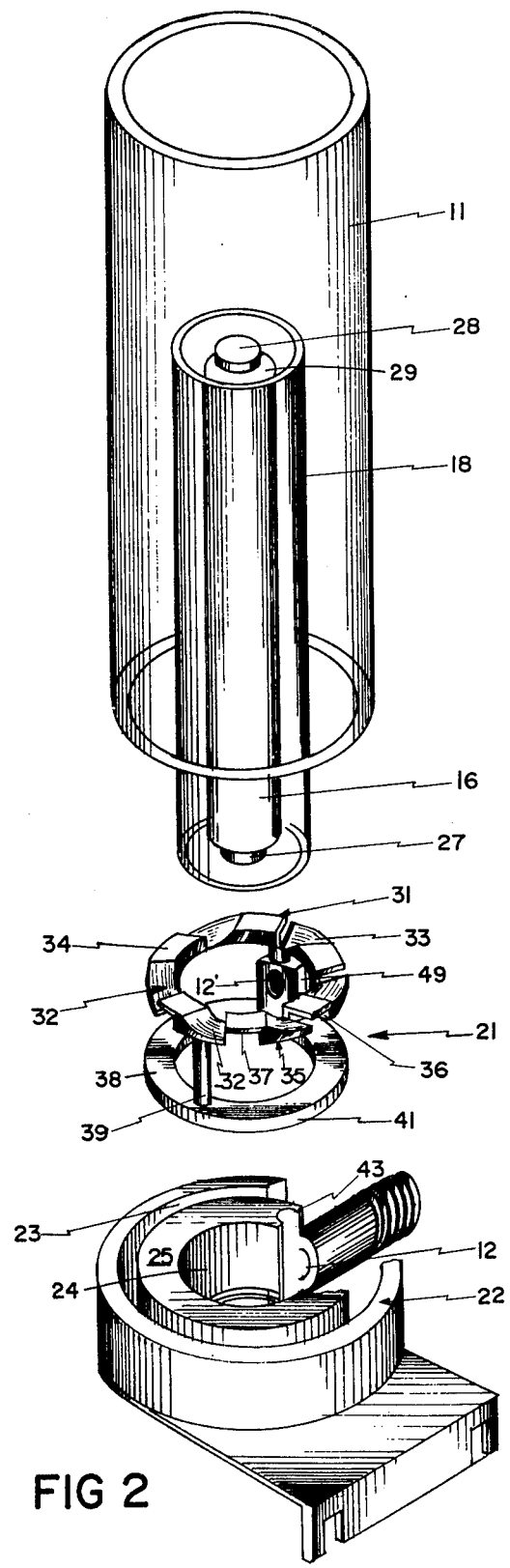
FIG. 2 is an exploded assembly drawing of a sterilizer illustrating the embodiment of the invention.

Referring to FIG. 2 the outer housing 11 is shown transparent, but it is not necessary that it be so. Mounted between the protective sheath 18 and the cylindrical housing 11 is a diffuser member 21 which surmounts an integral lower inflow end piece 22. The end piece 22 also defines the inlet channel 12.

The end piece 22 has an annular groove 23 and a central circular void 24 defined by an annular collar or uprise 25. Into the groove 23 the cylindrical housing 11 fits; it is secured therein by cement 26. Into central void 24 fits an end of the protective sheath 18; it is secured therein by cement 26 so as to provide a liquid seal thereabouts. The tube 16 projects into the central void 24 such that its free end having electrical contact 27 extending below the lower face of the end piece 22. In this manner a simple electrical connection (not shown) to the contact 27 may be made. The other electrical contact 28 of the tube 16 extends in a like manner above the upper end 29 of tube 16. Electrical energy may be directed to the tube 16 so that it may ignite to generate bacteriastat radiation.

The diffuser member 21 includes an annulus 31 composed of a plurality of non-overlapping vanes 32. The vanes are preferably individually shaped so that an upper portion thereof is a flat surface 34 and the lower portion thereof is also a flat surface 35. These surfaces are disposed in parallel planes essentially perpendicular to the central axis of the annulus 31. Disposed between these parallel surfaces, the upper flat surface 34 extends through a juncture into a graduated arcuate sheet curved surface 33 to terminate at a forward leading edge 38 of the subjacent lower flat surface of the same vane. The graduated sheet curved surface 33 follows, a continuous sheet curve along the loci of points between two boundaries; on the one hand, a flat plane disposed between the leading edge of the lower flat surface and the juncture, and on the other hand, a second plane which is disposed between the forward edge 38 (the leading edge super-adjacent the leading edge of the lower surface), and said juncture. Subadjacent a substantial extent of the upper surface but not extending to the juncture, is a notch 36 with a flat upper ceiling 37. The lower flat surface thus extends into this notch 36 at the opposite end from its leading edge. In essence, each vane is formed by a step consisting of first and second horizontal treads corresponding to elements 35 and 34, respectively, interconnected by a vertical riser (i.e., the vertical section of notch 36). Additionally, concave surface 33 extends from the leading edge of the first tread to the leading edge of the second tread such that the second tread and the vertical riser become an integral part of the concave surface. Each of the vanes is constructed as described and arranged in a non overlapping relation as the annulus 31.

The annulus 31 is attached through two upright members 39 and 40 to a lower flat annulus 41 which is cemented or otherwise attached to the upper surface of the annular collar 25. Preferably the upright member 40 includes a lower hollow portion 49 which defines an aperture or inlet orifice 12', in its face positioned, radially inward and communicating with inner channel 42.

The annular collar 25, in the end piece 22, also defines an uprising channel 43 which is an extension of and communicates with the inlet channel 12. These channels, 12, 43 and 42 are arranged in registry when the lower flat annulus 41 is affixed to the annular collar 25 as by cement. Preferably, if the members 21 and 22 are made of A.B.S. plastic an appropriate cement, as those skilled in the art will know, will suffice.

Figure 3:
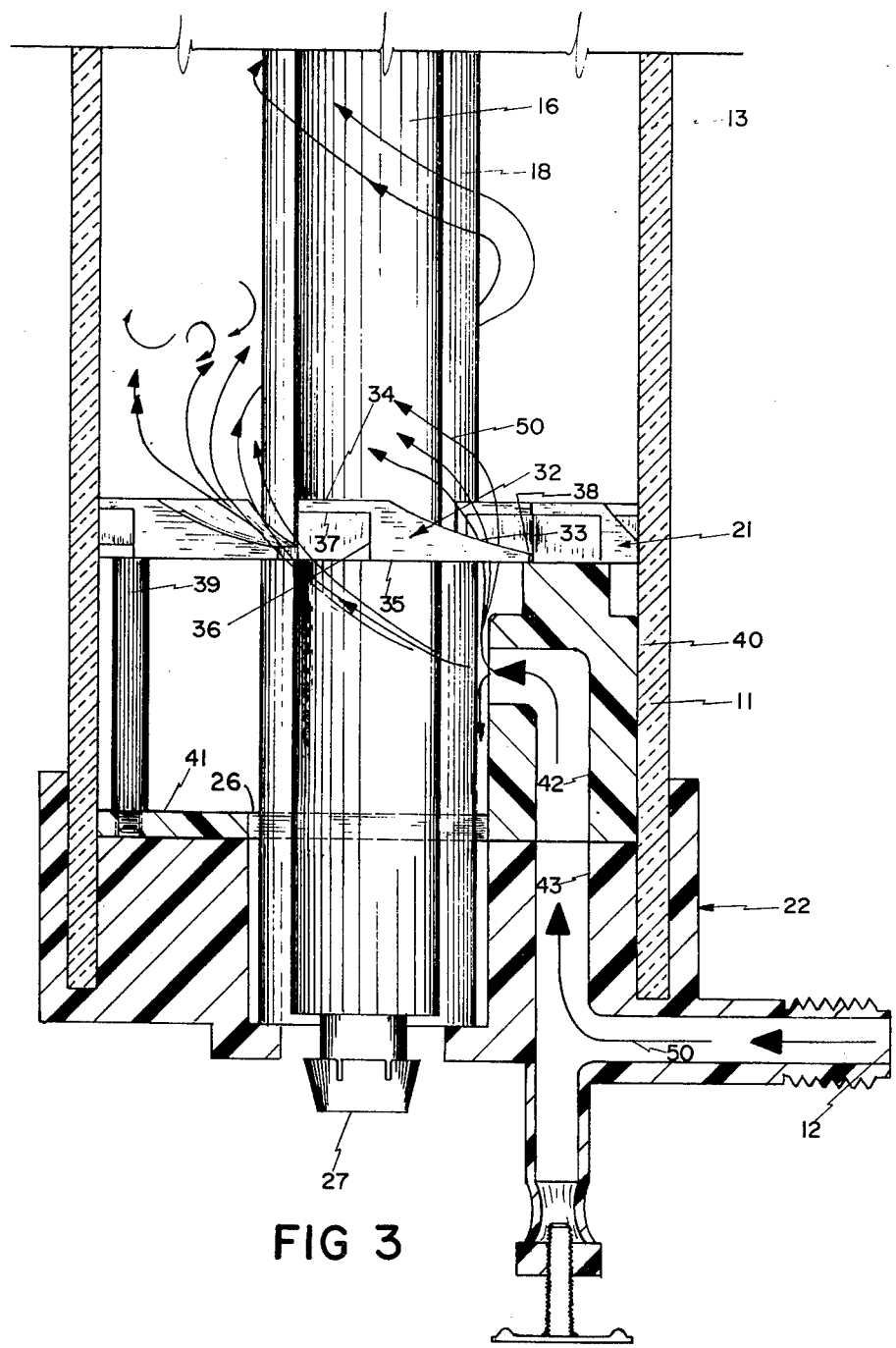
FIG. 3 is a section along lines II—II of FIG. 1.
Figure 4:
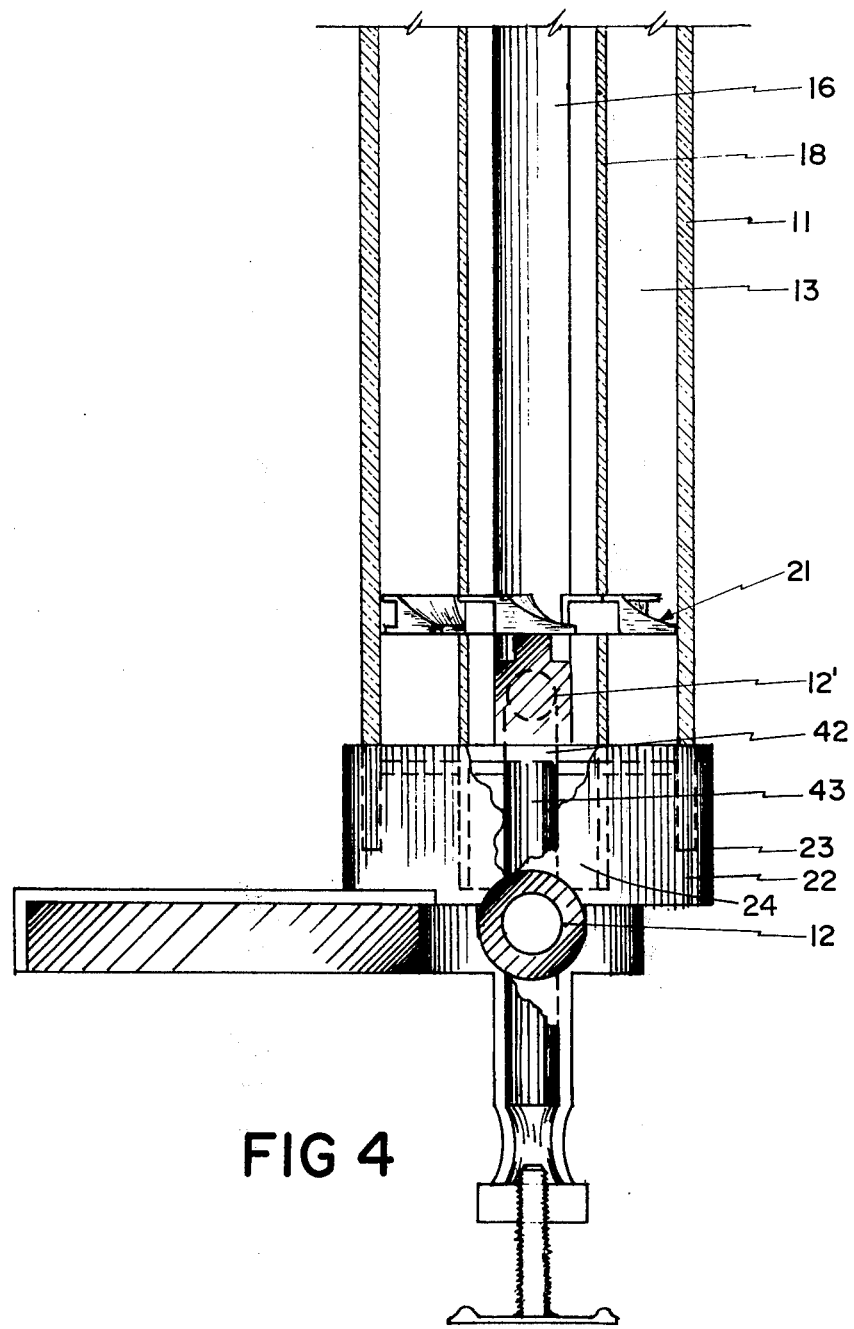
FIG. 4 is the side view looking into the inlet channel of the sterilizer, the exterior housing removed.

In assembly, see FIGS. 1 and 3, inflow fluid 50 flows into the inlet channel 12 up channel 43 into channel 42 and out the orifice 12'. The fluid, on exiting the orifice 12' immediately strikes the protective sheath 18 since it is opposite and in close proximity thereto and is deflected about it thereby destroying its undirectional jet momentum. The diffused fluid thence passes over the plurality of vanes 32 from underneath the vanes over the depending curved upper surfaces 33 of an adjacent vane, which diverts the flow into a helical turbulent path. This causes the liquid to pass through the sterilizer in turbulent fashion and hence to uniformly travel from chamber wall to protective glass sheath and thus exposed for a defined duration to the radiation from the flux tube 16 prior to its ultimate exit through the upper outflow channel 14.

Certain experiments have been conducted utilizing a 24 watt ultra-violet radiation tube 16 manufactured by the General Electric Company of U.S.A. at various flow rates for water with and without the diffusing member 21. The results of the experiments 1 and 2 are appended hereto. The expression "MPN" means most probable number and relates to the most probable number of organisms (bacteria) per 100 milliliters of liquid sample, after exposure to U.V. The second column represents the bacteria count before exposure to U.V.

The test water temperature averaged 6° centigrade (43° F) and all tests were conducted using standard unit testing procedures. The test organism was a 20 hour culture of E. coli in lactose broth in quantities estimated to give 25–40 bacteria per milliliter. Samples were taken after the unit was tested by the lactose fermentation test (5 tubes — 50 milliliters each). The following were the results.

Experiment 1

| Flow Rate (U.S. gal. per min.) | Plate Count Before Exposure to UV (per 100 ml.) | MPN After (per 100 ml.) | Lactose Tubes After (No. positive/5 tubes) |
| --- | --- | --- | --- |
| 3 | 3550 | <2.2 | 0/5 |
| 3 | 3400 | <2.2 | 0/5 |
| 3.5 | 3100 | <2.2 | 0/5 |
| 3.5 | 3400 | <2.2 | 0/5 |
| 4 | 3450 | <2.2 | 0/5 |
| 4 | 3450 | <2.2 | 0/5 |
| 4 | 3050 | <2.2 | 0/5 |
| 4 | 2750 | <2.2 | 0/5 |
| 4 | 4250 | <2.2 | 0/5 |
| 4 | 3450 | <2.2 | 0/5 |
| 4.5 | 3100 | <2.2 | 0/5 |
| 4.5 | 3100 | <2.2 | 0/5 |
| 4.5 | 3750 | <2.2 | 0/5 |
| 4.5 | 4250 | <2.2 | 0/5 |
| 5 | 3200 | <2.2 | 0/5 |
| 5 | 3100 | 2.2 | 1/5 |
| 5 | 3350 | <2.2 | 0/5 |

-continued

Experiment 1

| Flow Rate (U.S. gal. per min.) | Plate Count Before Exposure to UV (per 100 ml.) | MPN After (per 100 ml.) | Lactose Tubes After (No. positive/5 tubes) |
| --- | --- | --- | --- |
| 5 | 3100 | 2.2 | 1/5 |

Experiment 2

| Flow Rate (U.S. g.p.m.) | Plate Count Before Exposure to UV (per 100 ml) in Duplicate | | MPN After (per 100 ml) | Lactose Tubes After (No. positive/5 tubes) |
| --- | --- | --- | --- | --- |
| 3 | 4700 | 2600 | <2.2 | 0/5 |
| 3 | 2800 | 2800 | <2.2 | 0/5 |
| 3.5 | 3400 | 3700 | <2.2 | 0/5 |
| 3.5 | 3800 | 3700 | <2.2 | 0/5 |
| 3.5 | 3800 | 3500 | <2.2 | 0/5 |
| 3.5 | 3400 | 3500 | <2.2 | 0/5 |
| 3.5 | 4700 | 3800 | <2.2 | 0/5 |
| 4 | 3200 | 2600 | <2.2 | 0/5 |
| 4 | 3300 | 3300 | <2.2 | 0/5 |
| 4 | 3500 | 4200 | <2.2 | 0/5 |
| 4 | 3600 | 5200 | <2.2 | 0/5 |
| 4 | 4700 | 4700 | 2.2 | 1/5 |
| 4.5 | 3900 | 3100 | — | 5/5 |
| 4.5 | 4300 | 3700 | 5.1 | 2/5 |
| 4.5 | 3300 | 3900 | 5.1 | 2/5 |

Example 3
(Without defuser plate)

| Flow Rate (U.S. gal/min) | Plate Count Before Exposure to UV (per 100 ml) | MPN After (per 100 ml) | Lactose Tubes After (No. positive/5 tubes) |
| --- | --- | --- | --- |
| 1 | 3700 | <2.2 | 0/5 |
| 1 | 2500 | <2.2 | 0/5 |
| 1 | 1900 | <2.2 | 0/5 |
| 1 | 1775 | <2.2 | 0/5 |
| 1 | 1050 | <2.2 | 0/5 |
| 1 | 1000 | <2.2 | 0/5 |
| 1 | 775 | <2.2 | 0/5 |
| 1 | 650 | <2.2 | 0/5 |
| 1.5 | 4500 | <2.2 | 0/5 |
| 1.5 | 4400 | <2.2 | 0/5 |
| 1.5 | 4350 | <2.2 | 0/5 |
| 1.5 | 3900 | <2.2 | 0/5 |
| 1.5 | 3300 | <2.2 | 0/5 |
| 2 | 3800 | 5.1 | 2/5 |
| 2 | 2300 | >23 | 5/5 |
| 2 | 1900 | >23 | 5/5 |
| 2 | 1575 | 20 | 4/5 |
| 2 | 1450 | 4.0 | 2/5 |
| 2 | 1150 | <2.2 | 0/5 |
| 2 | 700 | 20 | 4/5 |
| 2 | 650 | 5.1 | 2/5 |
| 3 | 5050 | >23 | 5/5 |
| 3 | 2000 | >23 | 5/5 |
| 3 | 2000 | >23 | 5/5 |
| 3 | 850 | 16 | 4/5 |
| 3 | 750 | 16 | 4/5 |

Typical examples of the dimensions of the annulus 31 are as follows:

| | |
| --- | --- |
| Annulus 31 O.D. | 7.5 cm. |
| Annulus 31 I.D. | 4.0 cm. |
| Depth of Notch 36 | 0.6 cm. |
| Extent of Notch (ceiling 37 length) | 0.6 cm. |
| Extent of upper flat surface 34 | 1.5 cm. |
| Extent of lower flat surface 35 | 2.5 cm. |
| Overlap between surfaces 34 and 35 | 0.3 cm. |
| Distance between lower surface leading edge and forward edge 38 | ≅0.2 cm. |
| Exposure between forward edge 38 and ceiling 37 of forward vane | ≅0.3 cm. |

I claim:

1. In a fluid sterilization apparatus having a chamber defined by the space between an outer cylindrical housing and an ultraviolet radiation source coaxially mounted therein, the radiation source irradiating fluid flowing in the chamber from a source of fluid, and a fluid inlet channel at one end and a fluid outlet channel at the other end of the chamber, the improvement comprising: fluid flow deflector means having a chamber inlet orifice connecting said chamber to the inlet channel and disposed perpendicular to the longitudinal axis of and in close proximity to a portion of the radiation source, said portion of the radiation source being in the flow path of fluid emerging from said inlet orifice such that fluid flowing from the source of fluid through the inlet channel and emerging from the inlet orifice strikes a portion of the radiation source and is deflected into non-coincident flow paths in said chamber, and an annulus shaped device extending substantially transversely to and being coaxial with the longitudinal axis of the ultraviolet source and positioned in the chamber between the radiation source and the cylindrical housing, the annulus device having a plurality of rigid non-overlapping vanes and being positioned downstream of but in close proximity to the inlet orifice, each of said vanes being essentially in the form of a step extending in the direction of the longitudinal axis of the radiation source, said step being formed by first and second horizontal treads interconnected by a vertical riser, said first tread being spaced axially upstream of said second tread, and wherein said step is further formed by a concave surface extending between the leading edges of the first and second treads, said leading edges being those edges of the downstream portion of each tread which first contact the inflowing fluid, whereby said concave surface is integral with said vertical riser and said first tread, such that the fluid deflected into non-coincident flow paths in said chamber after striking the radiation source, passes over the concave surfaces of the vanes and is directed thereby into turbulent rotational paths flowing downstream through the chamber toward the fluid outlet channel.

* * * * *